(12) United States Patent
Moinet et al.

(10) Patent No.: US 7,285,681 B2
(45) Date of Patent: Oct. 23, 2007

(54) BIGUANIDE DERIVATIVES

(75) Inventors: Gerard Moinet, Orsay (FR); Daniel Cravo, Sartrouville (FR)

(73) Assignee: Merck Patent Gesellschaft, Darmstadt (DE)

( * ) Notice: Subject to any disclaimer, the term of this patent is extended or adjusted under 35 U.S.C. 154(b) by 173 days.

(21) Appl. No.: 10/472,229

(22) PCT Filed: Mar. 20, 2002

(86) PCT No.: PCT/EP02/03119

§ 371 (c)(1),
(2), (4) Date: Sep. 22, 2003

(87) PCT Pub. No.: WO02/074740

PCT Pub. Date: Sep. 26, 2002

(65) Prior Publication Data

US 2004/0092495 A1    May 13, 2004

(30) Foreign Application Priority Data

Mar. 21, 2001  (FR) .................................. 01 03846

(51) Int. Cl.
C07C 279/26   (2006.01)
A61K 31/155   (2006.01)
A61P 3/10     (2006.01)

(52) U.S. Cl. ....................... 564/233; 514/635

(58) Field of Classification Search ................. 564/233
See application file for complete search history.

(56) References Cited

U.S. PATENT DOCUMENTS

| | | | | |
|---|---|---|---|---|
| 2,937,173 | A | * | 5/1960 | Shapiro et al ............. 544/207 |
| 3,879,541 | A | | 4/1975 | Kabbe et al. |
| 3,960,949 | A | | 6/1976 | Ahrens et al. |
| 4,333,929 | A | | 6/1982 | Cantello |

FOREIGN PATENT DOCUMENTS

| | | |
|---|---|---|
| EP | 0034002 | 8/1981 |
| FR | 2085665 | 12/1971 |
| FR | 2696740 | 4/1994 |
| GB | 852584 | 10/1960 |
| JP | 61-41367 | * 2/1988 |

OTHER PUBLICATIONS

STN online, file CAPLUS, Acc. No. 1986:425797, Doc. No. 105:25797 (JP 61041367 (1986)), Abstract.*
Hawley's Condensed Chemical Dictionary (14th Ed. 2002) (http://www.knovel.com/knovel2/Toc.jsp?BookID=704&VerticalID=0), "epimer".*
Shapiro et al., Hypoglycemic Agents. III. N-alkyl-and Aralkylbiguanides. Journal of the American Chemical Society (1959), vol. 81, pp. 3728-3736.*
Wikipedia, the free encyclopedia (2006)(http://en.wikipedia.org/wiki/Stereoisomerism), pp. 1-3.*
The Merck Index (11th Ed. 1989), pp. 672, 1267, 1274, 1452.*
John W. James et al., "The Synthesis of some heterocyclic derivatives of biguanide with antibacterial activity", Journal of Medicinal Chemistry, vol. 11, No. 5, 1968, pp. 942-945.

* cited by examiner

Primary Examiner—Johann Richter
Assistant Examiner—Frank Choi
(74) Attorney, Agent, or Firm—Millen, White, Zelano & Branigan, P.C.

(57) ABSTRACT

The present invention relates to biguanide derivatives of formula (I), wherein R1, R2, R3 and R4 have the meanings as given in claim (1). Compounds are useful in the treatment of pathologies associated with hyperglycaemia, such as diabetes.

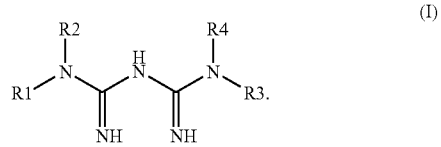

(I)

8 Claims, No Drawings

BIGUANIDE DERIVATIVES

The present invention relates to biguanide derivatives that are useful in the treatment of pathologies associated with hyperglycaemia, such as diabetes.

The World Health Organization has given the following definition of diabetes: "sugar diabetes (diabetes mellitus) is a condition of chronic hyperglycaemia which may result from many factors, some environmental and others genetic, often acting together".

Diabetes is a complex metabolic disease that is characterised by a dysfunction in the regulation of the blood glucose level (glycaemia). Whereas the normal blood glucose level is between 0.8 and 1 g/l, this level may be up to 3 to 4 g/l in the case of diabetes. The term diabetes is used for glycaemia exceeding 1.26 g/l. This hyperglycaemia modifies osmotic pressures and more globally ion exchanges throughout the body, impairing its overall functioning. This hyperglycaemia may be the cause of a number of serious disorders:
- cardiovascular disorders (hypertension, atherosclerosis)
- nephropathy
- neuropathy
- retinopathy
- dental diseases
- micro- and macroangiopathy
- coma for particularly high levels, possibly resulting in death.

The carbohydrate homeostasis is maintained in the body by means of the action of a set of hormones, the two most important of which are glucagon and insulin. The first makes it possible to control the release of glucose into the blood when glycaemia is low (physical effort), mainly by hepatic gluconeogenesis, whereas the second allows the absorption of glucose by all the peripheral cells (such as the muscles) and also the liver, which store it in the form of glycogen. It is thus these hormones that control the level of glycaemia.

In a healthy individual, the ingestion of food leads, after many steps of biodegradation (digestion) and absorption, to an increase in the blood glucose level (postprandial hyperglycaemia). This hyperglycaemia is only temporary: it gives the signal to the β cells of the islets of Langerhans in the pancreas to synthesize insulin. Since all the cells in the body contain insulin receptors, this results in a sequence of steps, the last of which is an increase in the number of glucose transporters at the surface of the cells, thus bringing about a decrease in the glycaemia.

Diabetes is, in point of fact, a combination of diseases of which hyperglycaemia is the common syndrome. Two types of diabetes are distinguished:

a) type I diabetes or insulin-dependent diabetes (IDD)

This is also referred to as juvenile-onset diabetes, ketosis-prone diabetes or brittle diabetes. It develops before the age of 30. Its origin is genetic: in most cases it is an autoimmune disease leading to the selective destruction of the β cells of the pancreatic islets of Langerhans from birth onwards. Insulin is then no longer synthesised and there is no longer any regulation of the blood glucos level.

Type I diabetes affects about 10 to 15% of diabetic patients. The only current treatment for this type of diabetes consists of regular injections of exogenous insulin.

b) type II diabetes or non-insulin-dependent diabetes (NIDD)

Type II diabetes is also known as lipogenous diabetes since, in 80% of cases, it is associated with obesity. This diabetes affects more mature individuals (from the age of 40). A genetic predisposition has been demonstrated, but the causative factors are clearly identified: excessively rich diet, lack of physical activity, sedentary lifestyle.

NIDD is characterised by two main anomalies, which are, firstly, a deficit in insulin secretion in response to glucose, and secondly, an impairment in tissue sensitivity to insulin. This insulin resistance is a characteristic trait of the disease, whether or not the diabetic patients are obese. It is observed both in the peripheral tissues (muscles, adipose tissues) and in the liver.

The cause of this insulin resistance is not entirely defined. It appears to arise from a dysfunction in the insulin receptor of the target cells or at a post-receptor level. It is also observed that, in the liver, the production of glucose by gluconeogenesis is higher than normal, whereas the absorption of glucose by the peripheral tissues is lower than normal. It is difficult to determine whether the deficiency in insulin secretion induces the desensitisation of the peripheral tissues or whether the insulin resistance causes a dysfunction in the β cells.

This type of diabetes is the most common: it concerns 85 to 90% of diabetics. In a first stage, a controlled diet and physical activity are recommended in order to re-establish normal functioning of glycaemia control, especially in obese patients. In the event of failure, recourse is then made to an oral treatment.

There are currently four major families of antidiabetic agents on the market:
- α-glucosidase inhibitors, such as acarbose or miglitol;
- "insulin sensitiser" compounds, such as rosiglitazone or pioglitazone;
- insulin secretors, such as gliclazide or nateglinide;
- biguanides, such as metformin.

The history of biguanides began at the start of the 19th century, but it was not until the 1940s that a therapeutic use for them was found (antimalarial, disinfectant, bactericidal, antidiabetic, etc. agents). Regarding the latter activity, three biguanides were launched on the market, namely buformin, phenformin and metformin. The first two were withdrawn from the market on account of severe lactic acidosis, and only metformin has been maintained on the market and is at the present time the highest-selling oral antidiabetic worldwide.

Despite all this, metformin has a number of weak points such as, for example, a mild lactic acidosis, an enormous tablet size when compared with other oral antidiabetic agents, and precautions for use in the case of the elderly.

Many documents describe the use of biguanides as hypoglycaemiant or anti-hyperglycaemiant agents. In this respect, reference may be made to the following documents:

FR 2 085 665, FR 2 132 396, J. Org. Chem., 1959, 81, 4635-4639, FR 2 696 740, EP 34 002.

Despite the abundance of literature regarding biguanide synthesis, only three have reached the commercial stage and only metformin has been maintained on the market.

Thus, the Applicant has discovered a novel biguanide family of the general formula (I)

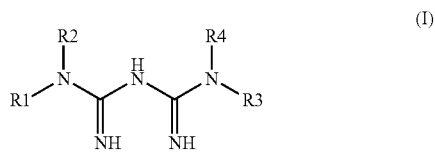

whose activity is comparable to or even greater than that of metformin, without having the unpleasant side effects.

It has also been demonstrated that this novel biguanide family has unexpected therapeutic effects not observed with metformin.

Unexpectedly, the compounds of formula I have properties which allow to induct or to increase the sorption (adsorption and/or absorption) of glucose by the muscle, also in absence of insulin.

The compounds of the invention are of the general formula (I) below:

$$\underset{R1}{\overset{R2}{\underset{|}{N}}}\underset{\underset{NH}{\|}}{C}\underset{\overset{H}{\underset{|}{N}}}{}\underset{\underset{NH}{\|}}{C}\underset{R3}{\overset{R4}{\underset{|}{N}}} \quad (I)$$

in which:
R1 and R2, which may be identical or different, represent a branched or unbranched ($C_1$-$C_6$)alkyl chain, or
R1 and R2 together form a 3- to 8-membered ring including the nitrogen atom to which they are attached,
R3 and R4 together form a ring selected from the group aziridine, pyrrolyl, imidazolyl, pyrazolyl, indolyl, indolinyl, pyrrolidinyl, piperazinyl and piperidyl including the nitrogen atom to which they are attached, and also the tautomeric, enantiomeric, diastereoisomeric and epimeric forms, the solvates and the pharmaceutically acceptable salts.

Among the branched or unbranched $C_1$-$C_6$ alkyl radicals that may especially be mentioned are the methyl, ethyl, propyl, isopropyl, butyl, sec-butyl, tert-butyl, pentyl and hexyl radicals.

3- to 8-membered rings including a nitrogen atom that may especially be mentioned are the aziridine, pyrrolyl, imidazolyl, pyrazolyl, indolyl, indolinyl, pyrrolidinyl, piperazinyl and piperidyl rings.

Preferably, R1 and R2, which may be identical or different, represent a ($C_1$-$C_6$)alkyl chain.

Even more preferably, R1 and R2 represent a methyl radical.

R3 and R4, together with the nitrogen atom to which they are attached, preferably form a pyrrolidine ring.

Thus, mention may be made more particularly of dimethylaminoiminomethylpyrrolidinecarboximidamide.

The invention also relates to the tautomeric forms and to the enantiomers, diastereoisomers and epimers of the compounds of the general formula (I).

The compounds of the general formula (I) contain basic nitrogen atoms that may be monosalified or disalified with organic or mineral acids.

A base of the formula I can be converted with an acid into the associated acid addition salt, for example by reaction of equivalent amounts of the base and of the acid in an inert solvent such as ethanol and subsequent evaporation. Suitable acids for this reaction are in particular those which yield physiologically acceptable salts. Thus inorganic acids can be used, e.g. sulfuric acid, nitric acid, halohydric acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or poly-basic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid. Salts with physiologically unacceptable acids, e.g. picrates, can be used for the isolation and/or purification of the compounds of the formula I.

The compounds of the formula (I) are prepared by simple and standard reactions readily available to the persons skilled in the art. By way of example, the following references illustrate these syntheses: FR 1 537 604, Ber., 1929 (62b), 1398, J. Org. Chem., 1959, 81, 3725-3728.

The compounds of the formula (I) are thus useful in the treatment of pathologies associated with hyperglycaemia.

The compounds of the invention especially show strong hypoglycaemiant activity.

The present invention thus also relates to pharmaceutical compositions comprising, as active principle, a compound according to the invention.

The pharmaceutical compositions according to the invention may be presented in forms intended for parenteral, oral, rectal, permucous or percutaneous administration.

They will therefore be presented in the form of injectable solutions or suspensions or multi-dose bottles, in the form of plain or coated tablets, sugarcoated tablets, wafer capsules, gel capsules, pills, cachets, powders, suppositories or rectal capsules, solutions or suspensions, for percutaneous use in a polar solvent, or for permucous use.

The excipients that are suitable for such administrations are cellulose derivatives, microcrystalline cellulose derivatives, alkaline-earth metal carbonates, magnesium phosphate, starches, modified starches and lactose for the solid forms.

For rectal use, cocoa butter or polyethylene glycol stearates are the preferred excipients.

For parenteral use, water, aqueous solutions, physiological saline and isotonic solutions are the vehicles that are the most suitable for use.

The dosage may vary within a wide range (0.5 mg to 1000 mg) depending on the therapeutic indication and the route of administration, and also the age and weight of the individual.

The present invention also relates to a method for treating diabetes by administering a composition comprising a therapeutic effective amount of at least one compound of formula (I):

$$\underset{R1}{\overset{R2}{\underset{|}{N}}}\underset{\underset{NH}{\|}}{C}\underset{\overset{H}{\underset{|}{N}}}{}\underset{\underset{NH}{\|}}{C}\underset{R3}{\overset{R4}{\underset{|}{N}}} \quad (I)$$

in which:
R1 and R2, which may be identical or different, represent a branched or unbranched ($C_1$-$C_6$)alkyl chain, or
R1 and R2 together form a 3- to 8-membered ring including the nitrogen atom to which they are attached,
R3 and R4 together form a ring selected from the group aziridine, pyrrolyl, imidazolyl, pyrazolyl, indolyl, indolinyl, pyrrolidinyl, piperazinyl and piperidyl including the nitrogen atom to which they are attached.

The present invention also relates to the use of compounds of formula (I) for manufacturing a pharmaceutical composition for treating diabetes.

The present invention also relates to a process to induct or to increase the sorption of glucose by the muscle, also in absence of insulin, by administering a composition comprising a therapeutic effective amount of at least one compound of formula (I):

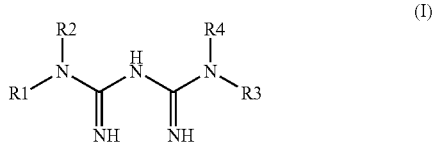

(I)

in which:

R1 and R2, which may be identical or different, represent a branched or unbranched ($C_1$-$C_6$)alkyl chain, or R1 and R2 together form a 3- to 8-membered ring including the nitrogen atom to which they are attached, R3 and R4 together form a ring selected from the group aziridine, pyrrolyl, imidazolyl, pyrazolyl, indolyl, indolinyl, pyrrolidinyl, piperazinyl and piperidyl including the nitrogen atom to which they are attached.

The present invention also relates to the use of the compounds of formula (I):

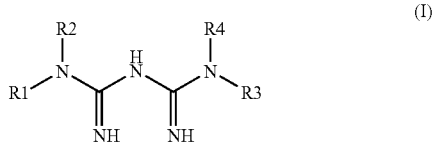

(I)

in which:

R1 and R2, which may be identical or different, represent a branched or unbranched ($C_1$-$C_6$)alkyl chain, or R1 and R2 together form a 3- to 8-membered ring including the nitrogen atom to which they are attached, R3 and R4 together form a ring selected from the group aziridine, pyrrolyl, imidazolyl, pyrazolyl, indolyl, indolinyl, pyrrolidinyl, piperazinyl and piperidyl including the nitrogen atom to which they are attached, for manufacturing a pharmaceutical composition for inducing or to increase the sorption of glucose by the muscle, also in absence of insulin.

Pharmaceutical compositions (medicaments) are particularly useful in patients having diabetes of type II or DNID, but also in all patients in need of improving sorption of glucose by muscle tissue.

Example 1 that follows illustrates the preparation of compounds of the formula (I).

Example 2 proves antidiabetic activity of compounds of formula (I) in rats.

Example 3 proves the effect of compounds of formula (I) on sorption of glucose by the leg of N5STZ rats in absence of insulin.

EXAMPLE 1

Dimethylaminoiminomethylpyrrolidinecarboximidamide Hydrochloride (Formula (I) in Which R1 and R2 Represent a Methyl Radical and R3 and R4 Form, Together with the Nitrogen, a Pyrrolidine Ring)

Pyrrolidine (30 g; 0.422 mol) is diluted in 50 ml of butanol and the medium is cooled. Concentrated hydrochloric acid (35.2 ml; 0.422 mol) is added slowly and, after stirring for 10 minutes, the solvent is removed under vacuum. The solid residue is taken up in butanol (40 ml) and dimethylcyanoguanidine (47.3 g; 0.422 mol) is added. The mixture is refluxed for 24 hours and then concentrated to dryness. The remaining solid is triturated with acetone (300 ml) to give 51.9 g (56%).

m.p.=205-207° C. (Köfler block)

$^1$H NMR (DMSO, 200 MHz): 1.90, m, 4H; 2.98, s, 6H; 3.37, m, 4H; 7.12, m, 4H $^{13}$C NMR (DMSO, 50 MHz): 25.22, 2 $CH_2$; 37.85, 2 $CH_3$; 47.30, 2 $CH_2$, 156.37 and 158.11, C=N

EXAMPLE 2

Study of the Antidiabetic Activity in N5STZ Rats

The oral antidiabetic activity of the compounds of the formula (I) was determined on an experimental model of non-insulin-dependent diabetes induced in the rats using steptozotocin.

The model of non-insulin-dependent diabetes is obtained in the rats by means of an injection of steptozotocin on the 5th day after birth.

The diabetic rats used are eight weeks old. The animals are housed, from the day of birth to the day of the experiment, in an animal house at a regulated temperature of 21 to 22° C. and subjected to a fixed cycle of light (from 7 a.m. to 7 p.m.) and darkness (from 7 p.m. to 7 a.m.). Their food consisted of a maintenance diet, and water and food were given "ad libitum", with the exception of fasting two hours before the tests, during which period the food is removed (post-absorptive state).

The rats are treated orally with the test product for four (D4) days. Two hours after the final administration of the product and 30 minutes after the animals have been anaesthetised with pentobarbital sodium (Nembutal®), a 300 μl blood sample is taken from the end of the tail.

By way of example, results obtained with compound 1 prepared above are collated compared with metformin in the following table. These results show the efficacy of the compounds of the formula (I) in reducing glycaemia in the diabetic animals. These results are expressed as a percentage change in the glycaemia on D4 (number of days of treatment) relative to D0 (before the treatment).

|  | 25 mg/kg | 50 mg/kg | 100 mg/kg |
| --- | --- | --- | --- |
| Metformin | −13 | −22 | −21 |
| Compound 1 | −6 | −23 | −36 |

EXAMPLE 3

Study of the Sorption of Glucose on the Perfused Leg of N5STZ Rats in Absence of Insulin with Compounds of Formula (I)

This study is performed with N5STZ rats. The model is characterized by hyperglycaemia, intolerance to glucose and insulin resistance. The model of non-insulin-dependent diabetes is obtained in the rats by means of an injection of steptozotocin on the 5th day after birth.

The diabetic rats used are eight to fourteen weeks old.

The animals are housed, from the day of birth to the day of the experiment, in an animal house at a regulated temperature of 21 to 22° C. and subjected to a fixed cycle of light (from 7 a.m. to 7 p.m.) and darkness (from 7 p.m. to 7 a.m.). Their food consisted of a maintenance diet, and water and food were given "ad libitum", with the exception of fasting 18 hours before the tests.

The rats are anaesthetised with pentobarbital and the left back leg is perfused (method by Ruderman, Biochem. J., 639-651, 1951) with a plug (cap) by Krebs-Ringer containing 8 mmol/L glucose and 0.5% BSA.

After 20 minutes of perfusion at 5 ml/min with a medium containing 8 mmol/glucose, the the back leg is perfused with a medium containing the compounds of formula (I) (10 μg/mL) and in absence of insulin. The sorption of glucose is calulated by calculating the difference of entering and leaving concentrations.

The results of this study are expressed in the following table:

|  | sorption of glucose μmol/g/l |
| --- | --- |
| control N5STZ | 19.23 ± 9.95 (n = 4) |
| metformin | 32.09 ± 7.25 (n = 4) |
| compound 1 | 116.08 ± 20.63 (n = 4) |

Unexpectedly, compounds of formula (I) induct (induce) sorption of glucose by the muscle in absence of insulin, whereas metformin has no effect.

The following examples relate to pharmaceutical preparations:

EXAMPLE A: INJECTION VIALS

A solution of 100 g of an active compound of the formula I and 5 g of disodium hydrogenphosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

EXAMPLE B: SUPPOSITORIES

A mixture of 20 g of an active compound of the formula I is fused with 100 g of soya lecithin and 1400 g of cocoa butter, poured into moulds and allowed to cool. Each suppository contains 20 mg of active compound.

EXAMPLE C: SOLUTION

A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. The solution is adjusted to pH 6.8, made up to 1 l and sterilized by irradiation. This solution can be used in the form of eye drops.

EXAMPLE D: OINTMENT 500 mg of an active compound of the formula I are mixed with 99.5 g of petroleum jelly under aseptic conditions.

EXAMPLE E: TABLETS

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE F: COATED TABLETS

Analogously to Example E, tablets are pressed and are then coated in a customary manner with a coating of sucrose, potato starch, talc, tragacanth and colourant.

EXAMPLE G: CAPSULES 2 kg of active compound of the formula I are filled into hard gelatin capsules in a customary manner such that each capsule contains 20 mg of the active compound.

EXAMPLE H: AMPOULES

A solution of 1 kg of active compound of the formula I in 60 l of double-distilled water is sterile-filtered, filled into ampoules, lyophilized under sterile conditions and aseptically sealed. Each ampoule contains 10 mg of active compound.

The invention claimed is:

1. A compound of formula (I)

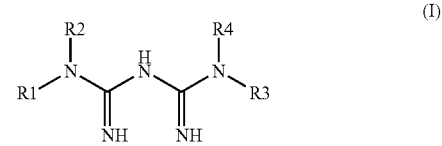

in which:
R1 and R2, which may be identical or different, are each methyl, ethyl, propyl, isopropyl, butyl, sec-butyl, tert-butyl, pentyl or hexyl;
R3 and R4, together with the nitrogen atom to which they are attached, form pyrrolidinyl; or the tautomeric forms thereof, or a solvate thereof or pharmaceutically acceptable salt thereof.

2. A compound according to claim 1, wherein R1 and R2 are each methyl.

3. A compound according to claim 1, which is Dimethylaminoiminomethylpyrrolidinecarboximidamide hydrochloride.

4. A compound according to claim 1, which is a tautomeric form thereof.

5. A compound according to claim 1, which is a solvate thereof.

6. A compound according to claim 1, which is a pharmaceutically acceptable salt thereof.

7. A compound of formula (I)
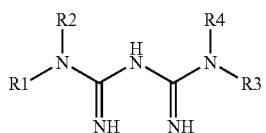
in which:
R1 and R2, which may be identical or different, are each methyl, ethyl, propyl, isopropyl, butyl, sec-butyl, tert-butyl, pentyl or hexyl;
R3 and R4, together with the nitrogen atom to which they are attached, form pyrrolidinyl; or pharmaceutically acceptable salt thereof.
8. A compound according to claim 7, wherein R1 and R2 are each methyl.
* * * * *